(12) United States Patent
Abascal Rubio et al.

(10) Patent No.: US 10,159,561 B2
(45) Date of Patent: Dec. 25, 2018

(54) DEVICE FOR TRAPPING THE END OF AT LEAST ONE FASCICLE OF SOFT MATERIAL IN A BONE TUNNEL

(71) Applicant: ABANZA TECNOMED, S.L., Pamplona (ES)

(72) Inventors: José Manuel Abascal Rubio, Pamplona (ES); Juan Abascal Azanza, Pamplona (ES)

(73) Assignee: Abanza Tecnomed, S.L., Pamplona (ES)

( * ) Notice: Subject to any disclaimer, the term of this patent is extended or adjusted under 35 U.S.C. 154(b) by 41 days.

(21) Appl. No.: 15/309,736

(22) PCT Filed: Jul. 21, 2014

(86) PCT No.: PCT/ES2014/070588
§ 371 (c)(1),
(2) Date: Nov. 8, 2016

(87) PCT Pub. No.: WO2015/169978
PCT Pub. Date: Nov. 12, 2015

(65) Prior Publication Data
US 2017/0143470 A1 May 25, 2017

(30) Foreign Application Priority Data
May 9, 2014 (ES) .................................. 201430688

(51) Int. Cl.
*A61B 17/86* (2006.01)
*A61F 2/08* (2006.01)

(52) U.S. Cl.
CPC ........ *A61F 2/0811* (2013.01); *A61B 17/8625* (2013.01); *A61B 17/8685* (2013.01);
(Continued)

(58) Field of Classification Search
CPC . A61B 17/86; A61B 17/8625; A61B 17/8635; A61B 17/864; A61B 17/8645;
(Continued)

(56) References Cited

U.S. PATENT DOCUMENTS

| 5,425,767 A * | 6/1995 | Steininger ............. A61F 2/0811 606/60 |
| 6,214,007 B1 * | 4/2001 | Anderson .......... A61B 17/0401 606/304 |

(Continued)

FOREIGN PATENT DOCUMENTS

| CN | 101094618 A | 12/2007 |
| WO | 01/056507 A1 | 8/2001 |
| WO | 2006/091278 A1 | 8/2006 |

*Primary Examiner* — Eric S Gibson
(74) *Attorney, Agent, or Firm* — Kramer Amado, P.C.

(57) ABSTRACT

The invention relates to a device for trapping the end of at least one fascicle (10) of soft material in a bone tunnel (1), comprising: a ferrule (100), a screw (200) and a washer (300), the ferrule comprising a proximal upper rim (140) and screwing elements (150), with a longitudinal axis (151) inclined α degrees in relation to the longitudinal axis (101) of the ferrule, and an inner thread (152) reciprocal to the outer thread (201) of the screw, the assembly being designed such that as the screw, with the washer, screws into the inner thread (152), the outer face (301) of the washer (300) approaches the inner face (142) of the proximal upper rim (140), an upper passage being formed between the two, via which the soft material projects, which is trapped in this way.

13 Claims, 8 Drawing Sheets

(52) U.S. Cl.
CPC .. *A61B 17/8695* (2013.01); *A61F 2002/0817* (2013.01); *A61F 2002/0882* (2013.01)

(58) Field of Classification Search
CPC .............. A61B 17/866; A61B 17/8685; A61B 17/8695; A61B 2017/8655
See application file for complete search history.

(56) References Cited

U.S. PATENT DOCUMENTS

| | | | |
|---|---|---|---|
| 6,517,579 B1 * | 2/2003 | Paulos | A61F 2/0811 606/232 |
| 7,255,700 B2 * | 8/2007 | Kaiser | A61F 2/0811 606/304 |
| 9,084,646 B2 * | 7/2015 | Sevrain | A61B 17/86 |
| 9,907,646 B2 * | 3/2018 | Beck, Jr. | A61F 2/0811 |
| 2006/0052787 A1 * | 3/2006 | Re | A61F 2/0805 606/191 |
| 2010/0268284 A1 * | 10/2010 | Bankoski | A61B 17/00234 606/308 |
| 2011/0313472 A1 * | 12/2011 | Yap | A61B 17/7064 606/305 |
| 2017/0165077 A1 * | 6/2017 | McDonnell | A61F 2/30907 |
| 2017/0215934 A1 * | 8/2017 | McDonnell | A61B 17/8685 |

* cited by examiner

DEVICE FOR TRAPPING THE END OF AT LEAST ONE FASCICLE OF SOFT MATERIAL IN A BONE TUNNEL

OBJECT OF THE INVENTION

The present invention relates to the field of traumatology, specifically to a device for trapping the end of at least one fascicle of soft material in a bone tunnel.

The object of the present invention is to provide a simple, precise and reliable device that allows trapping, with sufficient retaining force, without damaging soft tissue, the end of at least one fascicle of soft material in a bone tunnel.

BACKGROUND OF THE INVENTION

Tearing of soft material of the joints is very common, the most common being tearing of the anterior cruciate ligament (ACL) of the knee: grafts the ends of which are inserted in tibial and femoral bone tunnels are used for replacement thereof.

Compared to the use of bone-tendon-bone grafts, soft material grafts, autografts, allografts or synthetic grafts are used increasingly more often, which grafts at the femoral level are secured by means of transverse or suspension devices and at the tibial level they are secured by means of interference screws or washers with transtibial screws, which have the advantage of leaving the healing perimeter free and of providing a greater retaining force compared with interference screws.

In single tibial-femoral tunnel surgical techniques, in which the fascicles of soft material are suspended at the femoral level, the washer with a single transtibial screw is a very reliable solution at the tibial level; however, in new techniques that achieve restoring the helical anatomy of the original cruciate ligament by means of three femoral tunnels and three tibial tunnels, it would be necessary to use three long transtibial screws, which is not acceptable.

DESCRIPTION OF THE INVENTION

To be able to provide devices for trapping by means of a washer and screw which sufficiently clamp the fascicles of soft material, each of them in its own bone tunnel, without having to use long transtibial screws, the authors propose a new device for trapping by means of a ferrule which is introduced in the inlet opening of the bone tunnel, providing a screwing element for a frustoconical screw with an also frustoconical washer surrounding the head of the screw like a sleeve, the assembly configured such that as the screw, with the washer, screws into the ferrule, the outer face of the washer approaches the proximal inner face of a proximal upper rim existing in the ferrule, the soft material passing therethrough thereby being strongly trapped.

The new cone-shaped clamping configuration that is proposed allows exerting a great retaining force on the soft material, which notably increases on one hand because the ferrule is designed such that before the soft material is secured, it is folded over the inner face of the proximal upper rim, and on the other hand because it is contemplated that once the soft material is tensed and secured, the remaining material is cut and cauterized, forming a stump.

An additional objective of the present invention is to provide devices for trapping soft material that are easy to use, that do not damage the soft material and that do not project from the inlet opening of the bone tunnel.

DESCRIPTION OF THE DRAWINGS

To complement the description and for the purpose of helping to better understand the features of the invention according to a preferred practical embodiment thereof, a set of drawings is attached as an integral part of said description, in which the following is depicted.

PREFERRED EMBODIMENT OF THE INVENTION

Figure 1:
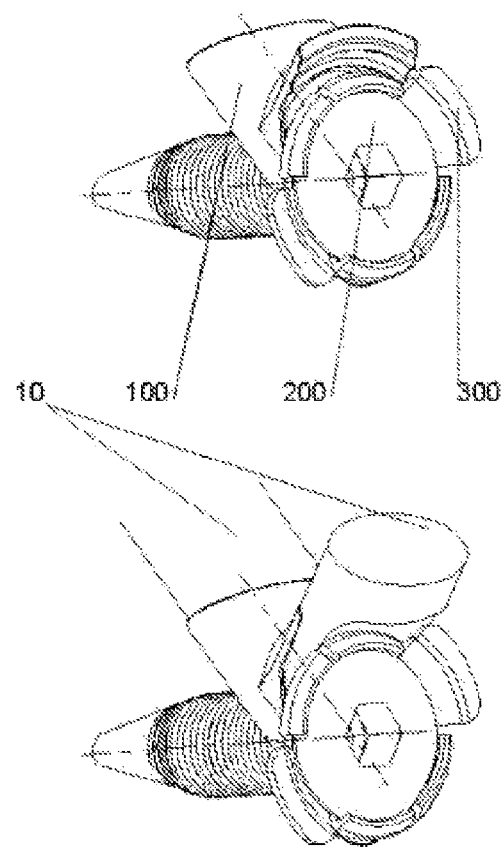
FIG. 1. In the upper part overall view of the device for trapping; in the lower part view of the device trapping a fascicle of soft material.
Figure 2:
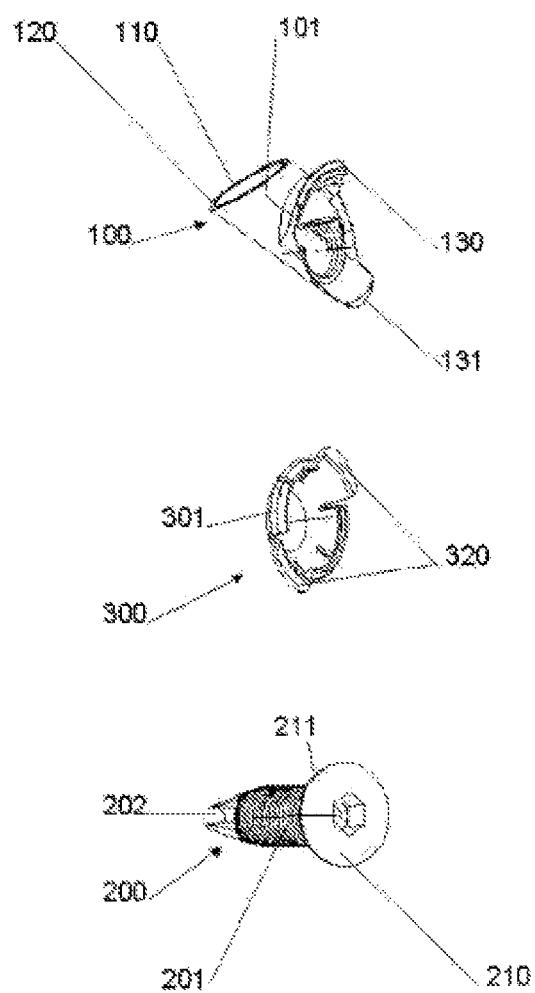
FIG. 2. Disassembled view of the device for trapping consisting of a ferrule, screw and washer.
Figure 3:
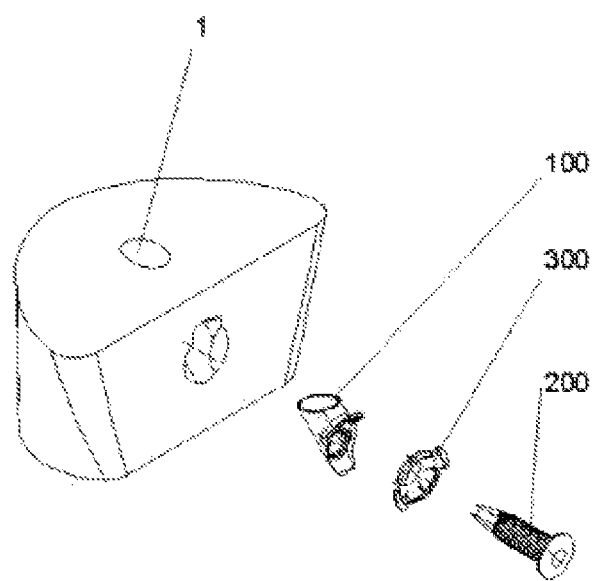
FIG. 3. Exploded view of the device for trapping and of the countersunk edge of the inlet opening into the bone tunnel in which the ferrule is incased.
Figure 4:
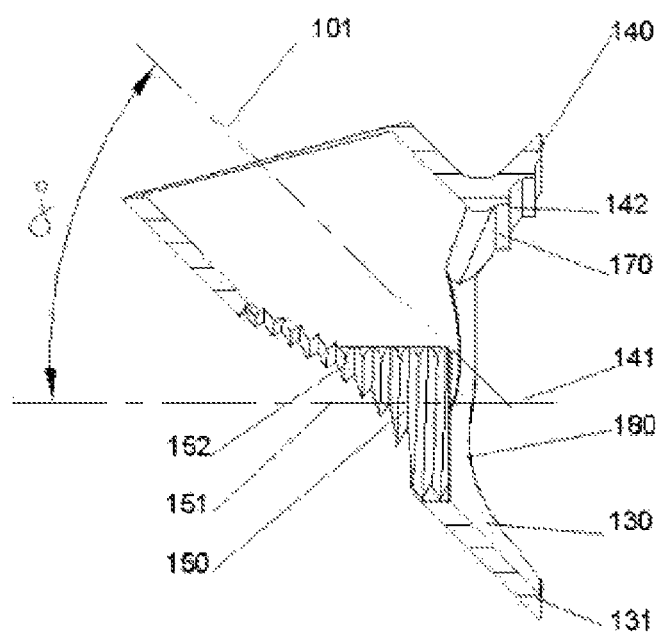
FIG. 4. Section view of the ferrule.
Figure 5:
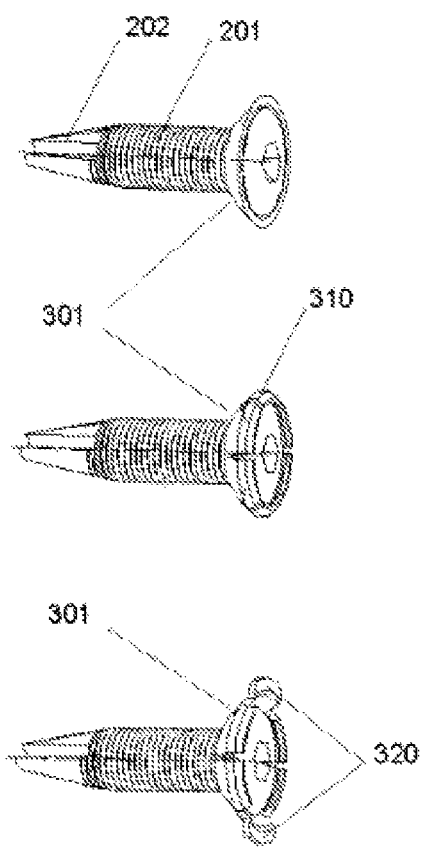
FIG. 5. In the upper part section view of the screw and washer; in the central part section view of the screw and washer with a rim; in the lower part section view of the screw and washer with a rim and with projections.
Figure 6:
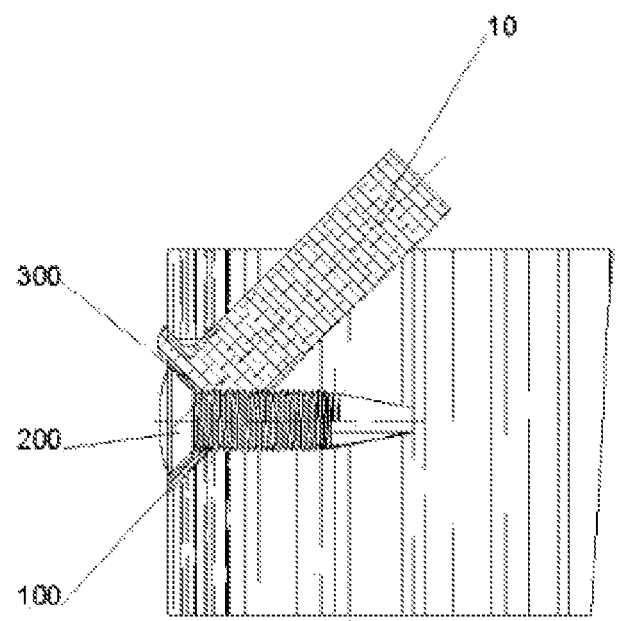
FIG. 6. Section view of the ferrule incased in the bone tunnel, with the screw and washer screwed together, trapping the soft material.
Figure 7:
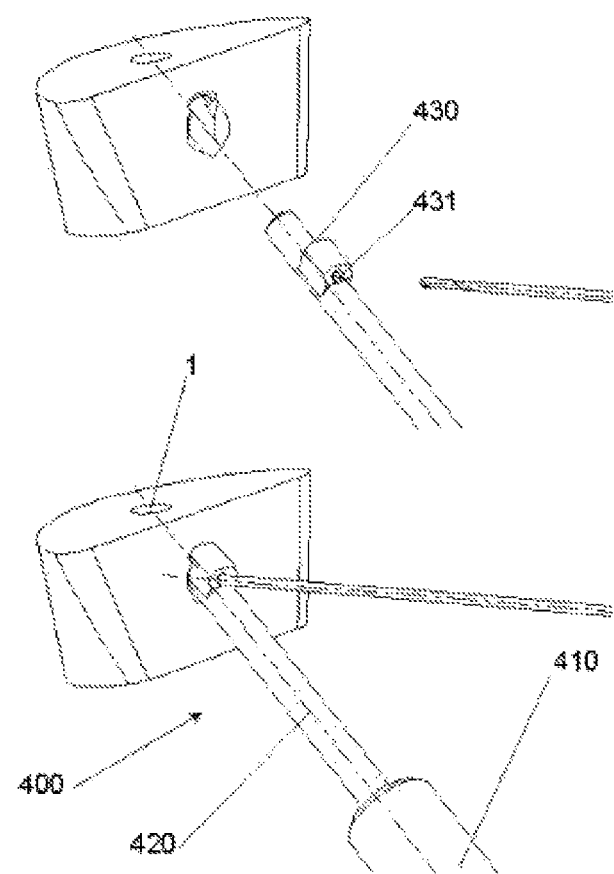
FIG. 7. In the upper part view of the milling key opposite inlet opening of the bone tunnel; in the lower part once it is introduced in the bone.
Figure 8:
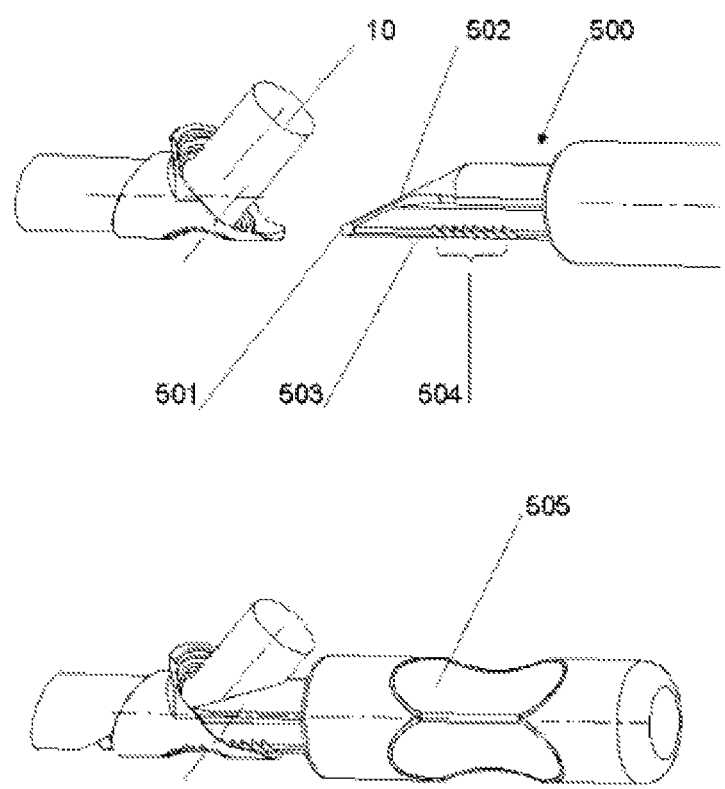
FIG. 8. In the upper part view of the wedge for trapping and of the ferrule; in the lower part view of the wedge introduced in the ferrule, trapping the soft material.

The preferred embodiment of the invention consists of a device for trapping the end of at least one fascicle (10) of soft material in a bone tunnel (1) comprising: a ferrule (100) having an outer diameter similar to that of the bone tunnel, a screw (200) and a washer (300), the three elements being shown assembled together in the upper part of FIG. 1 and disassembled in FIG. 2, the ferrule existing: a longitudinal axis (101), a longitudinal conduit (110), a distal end (120), a proximal end (130), a proximal edge (131), a proximal upper rim (140) and screwing elements (150), with a longitudinal axis (151) inclined α degrees in relation to the longitudinal axis (101) of the ferrule and inner thread (152) reciprocal to the outer thread (201) of the screw, the assembly being configured such that as the screw, with the washer, screws into the inner thread (152), the outer face (301) of the washer (300) approaches the inner face (142) of the proximal upper rim (140), an upper passage being configured between both of them, whereby the soft material projects, said soft material being thereby trapped, as shown in the lower part of FIG. 1 and in a section view in FIG. 6, both the ferrule and the screw and the washer being made from a biocompatible material or biocompatible materials; both the head (210) of the screw (200) and the washer (300) being configured in the preferred embodiment in frustoconical shapes of between 60° and 120°, preferably 90°, the washer (300) surrounding the perimeter (211) of the head (210) of the screw like a sleeve, the inner face (142) of the proximal upper rim (140) being configured in a reciprocal manner in an arched frustoconical or frusto-conoid shape, with a longitudinal axis (141) coinciding with the longitudinal axis (151) of the screwing element (150), the longitudinal axis (151) of which in turn has an inclination of between 30° and 60° in relation to the longitudinal axis (101) of the ferrule, preferably an inclination of 45°; the washer (300) optionally being prolonged into at least one projection (320) abutting with the cortical bone surrounding the inlet into the bone tunnel; there being grooves (170) on the inner face (142) of the proximal upper rim (140) for the purpose of reinforcing the trapping of soft material; there being on both sides of the proximal edge (131) of the ferrule (100) respective concave recesses (180) through which part of the head (210) of the screw (200) and of the washer (300) projects in the maximum clamping position; there being between the washer (300) and the head of the screw (200) fitting elements (310) preventing their separation, both at the time of their placement and when they are withdrawn, as shown in the lower part of FIG. 5; the screwing elements consisting of an inner thread (152) that is configured on the inner side and lower walls of the ferrule (100), truncated in the upper part thereof, there being in the screw a rounded-tip end (202); the distal end (120) of the ferrule (100) having an oblique ending, making the introduction thereof into the bone tunnel easier; there being for each ferrule (100) a milling key (400) with a handle (410), a rod (420) and a distal coupling (430) in which there is a milling guide consisting of a conduit (431) that maintains a relative position in relation to the longitudinal axis and to the countersinking of the bone tunnel identical to that of the longitudinal axis (151) of the ferrule (100) to be used; there being for each ferrule a provisional trapping wedge (500) for trapping soft material (10) consisting of a distal end at an acute angle (501), a smooth dorsal face (502) coming into contact with the soft material, a ventral face (503) with steps (504) incasing in the lower part of the inner thread (152) of the ferrule (100) and a proximal end with gripping elements (505) making handling thereof easier for the provisional securing of soft material and for the withdrawal thereof, which is used in lieu of the screw and washer for provisionally securing soft material in the ferrule during repeated bending and extending movements of the knee that are performed prior to the final tensing and trapping of each of the fascicles by means of the screw and the washer; the device preferably being made from a radio transparent polymer material.

Those skilled in the art will appreciate that variations and/or modifications in the device for trapping as described in this preferred embodiment are possible, without this entailing a departure from the scope thereof, therefore the description must be considered in an illustrative and non-limiting manner in any case.

The invention claimed is:

1. A device for trapping the end of at least one fascicle (10) of soft material in a bone tunnel (1), characterized in that it comprises:
    a ferrule (100) having an outer diameter configured to be similar to that of the bone tunnel,
    a screw (200) having a head and an outer thread (201), and
    a washer (300) having an outer face (301),
    the ferrule comprising:
        a hollow longitudinal conduit (110) extended along in a first longitudinal axis (101), the longitudinal conduit being configured to house said at least one fascicle,
        a distal end (120),
        a proximal end (130),
        a proximal edge (131),
        a proximal upper rim (140) having an inner face (142) and
        an opening (150) with an inner thread (152), extended along in a second longitudinal axis (151), with the second longitudinal axis (151) inclined α degrees in relation to the first longitudinal axis (101) of the ferrule, and the inner thread (152) being reciprocal to the outer thread (201) of the screw (200),
    wherein
        the device for trapping is configured such that as the screw (200), with the washer (300), screws into the inner thread (152), the outer face (301) of the washer (300) approaches the inner face (142) of the proximal upper rim (140), an upper passage being configured between both of them, whereby the soft material projects, said soft material being thereby trapped and housed in the hollow longitudinal conduit and the upper passage.

2. The device for trapping according to claim 1, characterized in that
    both the head (210) of the screw (200) and the washer (300) are configured in frustoconical shapes of between 60° and 120°,
    the washer (300) surrounding a perimeter (211) of the head (210) of the screw like a sleeve,
    the inner face (142) of the proximal upper rim (140) being configured in a reciprocal manner in an arched frustoconical or frusto-conoid shape, the second longitudinal axis (151) of which in turn has an inclination of between 30° and 60° in relation to the first longitudinal axis (101) of the ferrule (100).

3. The device for trapping according to claim 1, characterized in that there are grooves (170) on the inner face (142) of the proximal upper rim (140) for the purpose of reinforcing the trapping of soft material.

4. The device for trapping according to claim 1, characterized in that the proximal edge comprises two sides and on both sides of the proximal edge (131) of the ferrule (100) there are respective concave recesses (180) through which part of the head (210) of the screw (200) and of the washer (300) projects, a maximum clamping position being reached when the washer (300) comes into contact with an inner face of the proximal end (130) of the ferrule (100).

5. The device for trapping according to claim 1, characterized in that between the washer (300) and the head of the screw (200) there are fitting elements (310) preventing their separation.

6. The device for trapping according to claim 1, characterized in that that the inner thread (152) is configured on an inner side and lower walls of the ferrule (100), truncated in an upper part thereof.

7. The device for trapping according to claim 1, characterized in that the distal end (120) of the ferrule (100) has an oblique ending, making an introduction thereof into the bone tunnel easier.

8. The device for trapping according to claim 1, characterized in that for the ferrule (100) there is a provisional trapping wedge (500) for trapping soft material (10) consisting of an acute-angled distal end (501), a smooth dorsal face (502) coming into contact with the soft material, a ventral face (503) with steps (504) incasing in the lower part of the inner thread (152) of the ferrule (100) and a proximal end with gripping elements (505) making handling thereof easier both for a provisional securing of soft material and for a withdrawal thereof.

9. The device for trapping according to claim 1, characterized in that the ferrule is made from a polymer material.

10. The device for trapping according to claim 9, characterized in that the ferrule is made from a radio transparent polymer material.

11. The device for trapping according to claim 1, wherein the ferrule, the screw, and the washer are made from a biocompatible material or biocompatible materials.

12. The device for trapping according to claim 1, wherein the washer (300) is prolonged into at least one projection (320).

13. The device for trapping according to claim 1, wherein there is in the screw a central longitudinal conduit (202) through which a guide is introduced for screwing.

* * * * *